(12) United States Patent
Ketter et al.

(10) Patent No.: US 11,534,732 B2
(45) Date of Patent: Dec. 27, 2022

(54) PROCESS AND APPARATUS FOR QUENCHING A REACTOR EFFLUENT STREAM

(71) Applicant: UOP LLC, Des Plaines, IL (US)

(72) Inventors: Benjamin F. Ketter, Chicago, IL (US); Ernest J. Boehm, Hanover Park, IL (US); Michael J. Tobin, Elmhurst, IL (US); Joseph A. Montalbano, Elmhurst, IL (US); John J. Senetar, Naperville, IL (US); Joe Haas, Glenview, IL (US); Paul C. Steacy, Mt. Prospect, IL (US)

(73) Assignee: UOP LLC, Des Plaines, IL (US)

( * ) Notice: Subject to any disclaimer, the term of this patent is extended or adjusted under 35 U.S.C. 154(b) by 326 days.

(21) Appl. No.: 16/801,822

(22) Filed: Feb. 26, 2020

(65) Prior Publication Data
US 2021/0260554 A1     Aug. 26, 2021

(51) Int. Cl.
| | |
|---|---|
| C07C 7/09 | (2006.01) |
| B01J 8/24 | (2006.01) |
| B01J 8/18 | (2006.01) |
| B01D 5/00 | (2006.01) |
| C07C 1/20 | (2006.01) |

(52) U.S. Cl.
CPC ............ *B01J 8/24* (2013.01); *B01D 5/003* (2013.01); *B01D 5/0081* (2013.01); *B01D 5/0084* (2013.01); *B01J 8/1872* (2013.01); *C07C 7/09* (2013.01); *B01J 2208/00991* (2013.01); *C07C 1/20* (2013.01)

(58) Field of Classification Search
CPC .. B01J 2208/00991; B01J 8/1872; B01J 8/24; B01D 3/143; B01D 5/003; B01D 5/0081; B01D 5/0084; C07C 1/20; C07C 4/06; C07C 11/02; C07C 11/04; C07C 11/06; C07C 2529/035; C07C 2529/40; C07C 2529/83; C07C 2529/85; C07C 7/09
See application file for complete search history.

(56) References Cited

U.S. PATENT DOCUMENTS

| | | | |
|---|---|---|---|
| 6,403,854 B1 | 6/2002 | Miller | |
| 7,038,102 B2 * | 5/2006 | Van Egmond | ............ C07C 1/20 585/809 |

* cited by examiner

*Primary Examiner* — Sharon Pregler
(74) *Attorney, Agent, or Firm* — Paschall & Associates LLC; James C. Paschall

(57) ABSTRACT

A process and apparatus cool and remove catalyst from a hot vaporous reactor effluent stream by feeding the hot vaporous reactor effluent stream comprising catalyst and a first quench liquid stream to a first quench chamber. The hot vaporous reactor effluent stream is directly contacted with the first quench liquid stream to cool the hot reactor effluent stream and wash catalyst therefrom into the first quench liquid stream. The first quench liquid stream and the vaporous reactor effluent stream are passed together through a bed while disengaging catalyst from the vaporous reactor effluent stream and transferring catalyst into the first quench liquid stream.

14 Claims, 1 Drawing Sheet

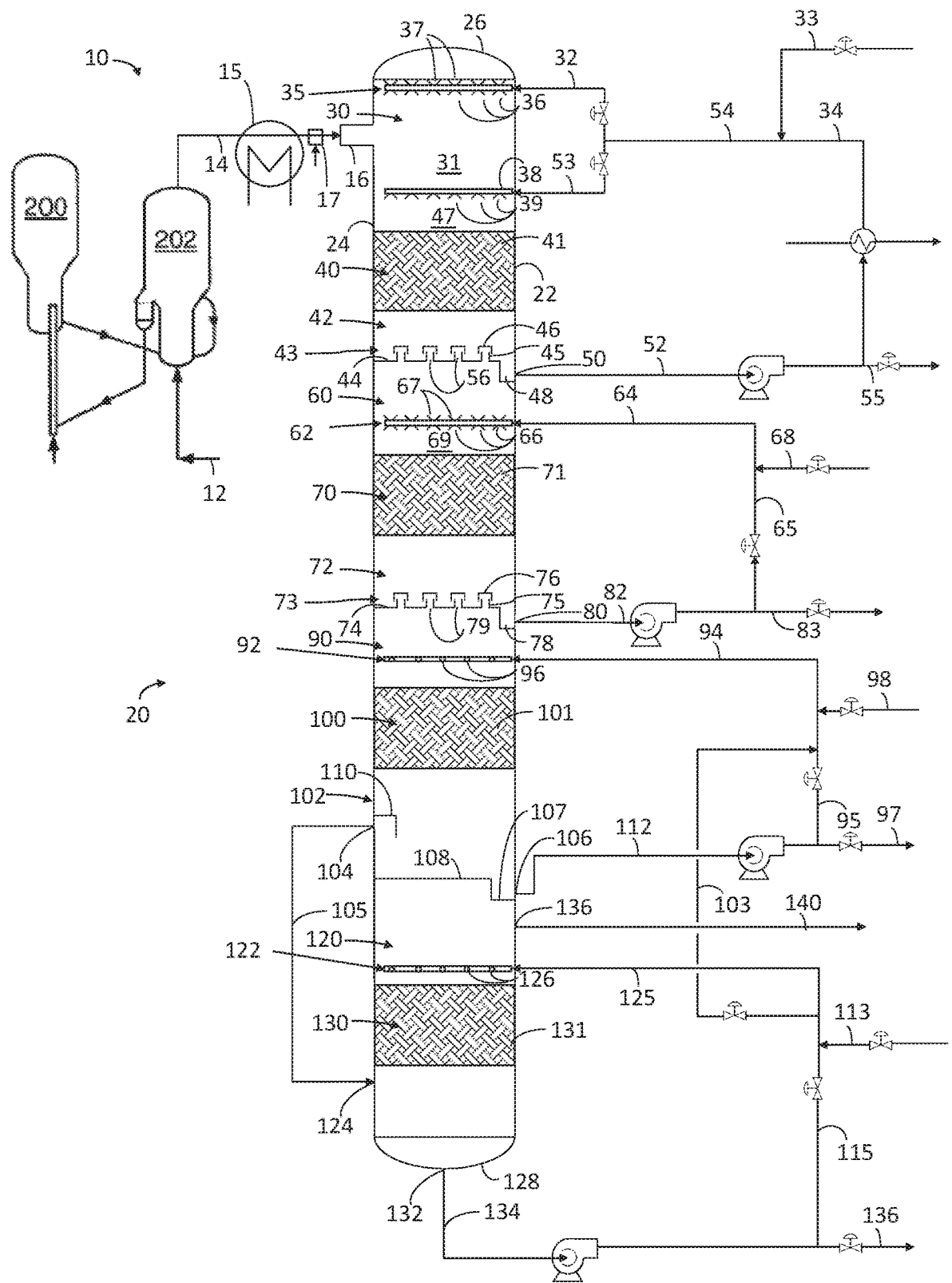

PROCESS AND APPARATUS FOR QUENCHING A REACTOR EFFLUENT STREAM

FIELD

The field is processes and apparatuses for quenching hot reactor effluent streams typically in the vapor phase and particularly effluents from a reactor that operates with a fluidized catalyst.

BACKGROUND

Fluidized catalytic reactions are conducted at elevated temperatures with fluidized catalyst that is free to move out of the reactor. Hot vaporous effluent exiting the fluidized catalytic, reactor caries a loading of catalyst fines despite equipment designed to retain catalyst in the reactor or remove it from reactor effluent. Downstream equipment is necessary to cool the reactor effluent and to remove catalyst therefrom. Fluidized catalytic processes include fluid catalytic cracking (FCC), methanol-to-olefins (MTO), toluene methylation and paraffin dehydrogenation.

The conversion of oxygenates to olefins such as in a WO process takes place at a relatively high temperature, generally higher than about 250° C., and preferably higher than about 300° C. In the conversion of oxygenates to olefins, a significant amount heat is released in the highly exothermic reaction. Because the reactor effluent typically is at a higher temperature than the temperature of feedstock, many methods and schemes have been proposed to manage the heat of reaction generated from the process.

In a conventional MTO process, a quench tower is utilized to cool hot reactor vaporous effluent by contact with water. MTO quench towers operate with vaporous effluent entering the bottom of the quench tower and quenching water added to the top of the tower and counter current contact therebetween.

Processes and equipment are sought to quench the hot vaporous reactor effluent while recovering catalyst from the effluent.

BRIEF SUMMARY

A process and apparatus are disclosed for cooling and removing catalyst from a hot vaporous reactor effluent stream. Hot vaporous reactor effluent stream comprising hydrocarbon reactor products, water and fines catalyst, and a first quench liquid stream are fed to a first quench chamber. The hot vaporous reactor effluent stream is directly contacted with the first quench liquid stream to cool the hot reactor effluent stream and wash catalyst therefrom transferring it into the first quench liquid stream. The first quench liquid stream and the vaporous reactor effluent stream are passed together through a bed while disengaging catalyst from the vaporous reactor effluent stream and transferring catalyst into the first quench liquid stream.

Additional details and embodiments of the disclosure will become apparent from the following detailed description.

BRIEF DESCRIPTION OF THE DRAWINGS

The FIGURE is a schematic elevational view of a disclosed process and apparatus.

DETAILED DESCRIPTION

The present disclosure pertains to a new reactor effluent quench tower that may serve one to three purposes: quench and desuperheat the reactor effluent on the outlet of the reactor effluent cooler; remove fine particulate catalyst that was not removed from the reactor effluent stream by cyclones or other equipment in the reactor; and neutralize and remove the byproduct organic acids, such as acetic acid and formic acid, that are generated in the upstream catalytic reaction. The present disclosure of an improved quench tower utilizes co-current flow to allow for higher gas velocities and smaller column diameters, resulting in lower capital costs. Higher gas velocities in the neutralization section will allow for higher mass transfer rates. The improved quench tower facilitates co-current quench and particulate removal while maximizing wetting on all column surfaces. The co-current flow may be down flow by feeding the liquid and the vaporous effluent both near the top of the column or chamber.

Conventional countercurrent quench towers may exhibit high fouling on the underside of trays in the bottom section of the tower, causing high differential pressure which can result in tray blowout. The conventional quench tower may also experience high fouling in the middle and top sections, owing to poor catalyst removal in the bottom sections. Once the catalyst fines reach the middle and top sections and are contacted by the caustic soda that is intended to neutralize the organic acids, the caustic soda dissolves the catalyst binder, causing it to foul severely. The conventional quench tower may also not properly neutralize organic acids, allowing these acids to be sent to downstream equipment that do not contain metallurgy designed for organic acid services. Non-agitated spots on trays, accumulators, and walls may agglomerate catalyst particles leading to fouling and clogging.

The improved quench tower will prevent excessive fouling, reducing the risk of fouling accumulation potentially causing damage to the tower internals and leading to poor performance.

The present disclosure of a quench tower may be used in an oxygenate to olefin process such as the MTO process and may be used in other fluidized catalytic technologies such as toluene methylation, paraffin dehydrogenation and FCC. However, the process and apparatus will be described herein in the context of a MTO unit.

Turning to the FIGURE illustrating a process and apparatus 10, a superheated feed stream in line 12 is fed to an oxygenate conversion reactor 202 that operates with fluidized catalyst. A hot vaporous reactor effluent stream in line 14 is withdrawn from an oxygenate conversion reactor 202 which periodically or continuously circulates fluidized catalyst in a conventional manner to the regeneration zone 200 to maintain the selectivity and the conversion desired. Reactor 202 is maintained at effective conditions for the conversion of the oxygenate to produce light olefin products. The hot vaporous reactor effluent stream may comprise light olefins, water, impurities, unreacted oxygenates, and catalyst fines. Catalyst fines may range between 0.05 and 0.3 wt % of the vaporous reactor effluent stream.

The hot vaporous reactor effluent stream in line 14 may be preliminarily cooled in a reactor effluent heat exchanger 15 to recover heat before it is passed to a quench tower 20. Moreover, a low pressure drop desuperheater 17 may be located on line 14 downstream of the reactor effluent heat exchanger 15 to partially desuperheat the vaporous reactor effluent stream upstream of the quench tower 20 and reduce the magnitude of turbulence in the quench tower 20 by reducing vapor flashing and temperature at the inlet to the quench tower. This desuperheating may be accomplished with water contact in the desuperheater 17.

The quench tower 20 may be a single vessel 22, but it may be broken up into a plurality of vessels. By comprising the quench tower 20 in a plurality of separate vessels, at least the first vessel can be reduced in height relative to a single vessel 22 housing all of the chambers which would allow the vaporous reactor effluent stream to be transported in line 14 at a downward angle to assure downward drainage of the catalyst fines. Hence, even by routing the vaporous reactor effluent stream to the top of the first vessel of the quench tower 20, the line 14 may be made to slope downwardly from reactor to an inlet nozzle 16 of the quench tower. Stacking downstream chambers of the quench tower 20 may be permissible since most of the catalyst fines may be removed in the shorter first vessel. Moreover, by breaking the quench tower into a plurality of vessels, one of the plurality of vessels could be taken offline for cleaning or maintenance, while the other vessels in the plurality stay online to allow operation to proceed without losing operating revenue. In an aspect, the quench tower 20 will be described as comprising a single vessel 22 comprising an outer wall 24 and a plurality of chambers in a single vessel 22.

In an embodiment, the quench tower 20 comprises four chambers. A first quench chamber 30 may be at the top 26 of the single vessel 22 and comprise a desuperheating zone 31. The top 26 may comprise a hemispherical head. The first quench chamber 30 may be defined by a top of the single vessel 22, the outer wall 24 and a vapor liquid separator 42. The reactor effluent inlet nozzle 16 may comprise a nozzle that is located in the wall 24, but it may located in the top 26 of the quench tower 20. The reactor effluent inlet nozzle 16 may be in downstream communication with the reactor 202 and feed the hot vaporous reactor effluent stream to the first quench chamber 30 and the quench tower 20. The term "communication" means that fluid flow is operatively permitted between enumerated components, which may be characterized as "fluid communication". The term "downstream communication" means that at least a portion of fluid flowing to the subject in downstream communication may operatively flow from the object with which it fluidly communicates. The reactor effluent inlet 16 may or may not contain an inlet mechanical distributor device.

A quench liquid stream distributor 35 with an array of lower liquid spray nozzles 36 is located directly above the reactor effluent inlet nozzle 16 or directly below the nozzle if the nozzle is in the top 26. The lower liquid spray nozzles 36 feed and spray a first quench liquid from a line 32 downwardly onto the hot vaporous reactor effluent stream to desuperheat the hot vaporous reactor effluent stream. The first quench liquid stream in line 32 may comprise cooled pumparound water in line 34 and make-up stripped water in line 33 which combine to provide a desuperheat quench stream in line 54. The first quench liquid stream may have a temperature in the range of about 50° C. to about 65° C. The spray nozzles typically have a conical spray pattern and an advantageous droplet size distribution to maximize capturing particulates in the aqueous phase. Lower liquid spray nozzles 36 will be pointed downwardly. However, upper inlet spray nozzles 37 on the quench liquid stream distributor 35 will be pointed upwardly at the top 26 of the vessel 22 to prevent fine catalyst particle accumulation on the top 26 of the vessel.

The quantity of water pumped to the liquid spray nozzles 36, 37 will be 100-110% of the water required to bring the superheated reactor effluent vapor to its dew point. The lower spray nozzles 36 will be located at a recommended minimum distance above the reactor effluent inlet nozzle 16, and the upper spray nozzles 37 will be located at a recommended minimum below the top 26 of the vessel 22 required to fully develop the intended spray pattern. The typical clearance is about 0.3 to about 3 meters. A desuperheating zone 31 is located directly below the reactor effluent inlet nozzle 16 in which the first quench liquid stream will contact the hot vaporous reactor effluent stream to cool and desuperheat the vaporous hot reactor effluent stream and wash catalyst therefrom into the first quench liquid stream, thereby leaving the vaporous hot reactor effluent stream in the vapor phase.

In the first quench chamber 30, two liquid distributors may be used, a first quench distributor 35 for desuperheating the hot reactor effluent while capturing catalyst into the quench liquid. A first wetting distributor 38 distributes a first wetting liquid to further capture catalyst and ensure adequate wetting in a bed 40 to capture catalyst into the liquid phase in the bed.

Below the desuperheating zone 31, a first departiculation zone 47 is provided below the first wetting distributor 38 for catalyst removal. The first wetting distributor 38 with a set of lower liquid spray nozzles 39 pointed downwardly at a first bed 40, will feed and spray the first wetting liquid stream from a line 53 onto the bed. The lower liquid spray nozzles 39 are designed to create water droplets sized to capture catalyst particles as well as wetting the first bed 40 to enable capture of particulates into the liquid phase. The first wetting liquid stream may have a temperature in the range of about 50° C. to about 65° C.

The bed 40 may comprise a structured packing 41 which may comprise a grid of adjoining metal corrugated plates stacked in layers to foster circuitous travel through the bed to promote contacting between the liquid and the vapor. The packing 41 in the bed 40 should be fouling-resistant for severe service. Suitable packing should have minimal horizontal surfaces to minimize catalyst hold up such as with a surface area per unit volume of less than about 90 $m^2/m^3$, suitably less than about 70 $m^2/m^3$ and preferably less than about 40 $m^2/m^3$. Suitable structured packing may have a free volume of at least 95%. Random packing may also be used in the bed 40, but it should be fouling resistant. Typical examples of structured packing that may be used are Proflux by Koch Glitsch, Raschig Grid Packing and Mellagrid by Sulzer.

The wetting liquid is sprayed onto the bed for the purpose of wetting the packing. The wetting liquid in line 53 may comprise cooled pumparound water in line 34 and make-up stripped water in line 33. The flow rate to these nozzles 39 will be designed such that the bed will be sufficiently wet to prevent particle accumulation and fouling in the bed 40. Adequate wetting of the packing 41 will also maximize catalyst wetting and capture into the liquid phase throughout the packed bed 40. The desuperheating zone 31 and perhaps the reactor effluent inlet nozzle 16 may be interposed between the first quench liquid stream distributor 35 and the first wetting liquid stream distributor 38. The first wetting liquid stream distributor 38 may be spaced apart below the reactor effluent inlet nozzle 16. The nozzles 39 will be located at a minimum distance above the bed 40 to permit full development of the intended spray pattern before reaching the bed. The quench liquid stream distributor 35 and the reactor effluent inlet 16 and perhaps the wetting liquid stream distributor 38 should all be disposed on the same side of the bed 40 and preferably above the bed 40 to, in an embodiment, provide downward flow through the bed.

The first quench liquid stream, the wetting liquid stream and the vaporous reactor effluent stream pass together through the bed 40 in a co-current flow arrangement while disengaging catalyst from the vaporous reactor effluent stream to reduce its catalyst loading and transferring the catalyst into the quench liquid stream and the wetting liquid stream to increase its catalyst loading. Particle transfer from the vaporous reactor effluent stream into the quench liquid stream and the wetting liquid stream and additional heat exchange will occur in the bed 40 below the wetting liquid stream distributor 38.

The first quench liquid stream and the first wetting liquid stream with an increased loading of catalyst is separated in the vapor liquid separator 42 below the bed 40 from the vaporous reactor effluent stream with a decreased loading of catalyst at the bottom of the first quench chamber 30. A chimney tray 44 may be used as the vapor liquid separator 42 to make the separation. The chimney tray 44 may have one or more chimneys 43 each comprising an open vertical tube 45 extending upwardly from the tray aligned with a respective opening or vapor passage 56 in the tray with a cap 46 over a respective open tube. The tube 45 allows a liquid level to develop on the tray 44 which is designed to rise to below the top of the open tube. The cap 46 on the tube 45 prevents descending liquid from passing through the chimney 43 and through vapor passage 56 in the tray 44. Normally only vaporous reactor effluent passes in a circuitous route through the chimney 43 from the first quench chamber 30 through vapor passage 56 to below the tray 44 and/or to a downstream chamber.

A well 48 at a periphery of the tray 44 collects the liquid which is discharged from a quench liquid stream outlet 50 from the first quench chamber 30. The first quench liquid stream and the wetting liquid stream each with an increased loading of catalyst are, perhaps together, removed in line 52 from the liquid outlet 50 and are pumped around and cooled to provide the cooled pump around stream in line 34. A portion of the first quench liquid stream and the first wetting liquid stream removed at outlet 50 is purged to water treatment in purge line 55. The loading of catalyst fed to the first chamber 30 in the first quench liquid stream and the first wetting liquid stream is determined by the proportions of water added from lines 33 and 34 to make the desuperheat quench stream in line 54 which depends on the proportion of the first quench liquid stream and the first wetting liquid stream purged in line 55.

The chimney tray 44 may require agitation or flushing to prevent accumulation of catalyst and disruption of pump performance. Extra nozzles and liquid inlet devices may be provided in the vicinity of the chimney tray 44 to reduce the risk of particulate buildup in stagnant zones of the tray which may otherwise agglomerate catalyst. The chimney tray 44 may be sloped or slanted toward the well 48 to facilitate particle collection to reduce the risk of disruption of pump performance.

In an embodiment, a desuperheated vaporous reactor effluent stream with a decreased loading of catalyst is passed through at least one vapor passage 56 to a downstream chamber. In an embodiment, the next immediately downstream chamber is a second, departiculation chamber 60. The second, departiculation chamber 60 comprises a second wetting stream distributor 62 proximate to and preferably below the vapor passage 56 for admitting the vaporous reactor effluent stream to the second chamber 60. The second wetting stream distributor 62 comprises an array of lower liquid spray nozzles 66 which will feed and spray a second wetting liquid from a line 64 onto a bed 70 and the vaporous reactor effluent stream to further remove remaining catalyst from the vaporous reactor effluent stream.

Below the vapor passage 56, a second departiculation zone 69 is provided below the second wetting distributor 62 for catalyst removal. The second wetting liquid stream in line 64 may comprise pumparound water in line 65 and make-up stripped water in line 68 which combine to provide the second wetting liquid stream in line 64. The lower liquid spray nozzles 66 are designed to create water droplets sized to capture catalyst particles as well as wetting the second bed 70 to enable capture of particulates into the liquid phase. The second wetting liquid stream may have a temperature in the range of about 50° C. to about 65° C. The liquid spray nozzles 66 typically have a conical spray pattern and an advantageous droplet size distribution to maximize capturing particulates in the aqueous phase. Lower liquid spray nozzles 66 will be pointed downwardly. However, upper liquid spray nozzles 67 on the distributor 62 will be pointed upwardly at the top of the second chamber 60 in an aspect at the bottom of the vapor liquid separator 42 to prevent fine catalyst particle accumulation on the top of the second chamber 60 or the bottom of the vapor liquid separator 42.

The upper liquid spray nozzles 67 will be located at a minimum distance below the top of the second chamber 60 which may be the vapor-liquid separator 42 and the lower liquid spray nozzles 66 will be located at a minimum distance above the bed 70 required to fully develop the intended spray pattern. The typical clearance is about 0.3 to about 3 meters. The bed 70 may comprise a packing 71 which may comprise a grid of adjoining metal corrugated plates stacked in layers to foster circuitous travel through the bed to promote contacting between the liquid and the vapor. The packing 71 in the bed 70 should be fouling-resistant, structured packing for severe service. Random packing may also be used in the bed 70, but it should be fouling resistant. The packing 71 may be the same as that used in first bed 40.

The wetting liquid is sprayed onto the bed for the purpose of wetting the packing. The flow rate to the downward nozzles 66 will be designed such that the bed 70 will be sufficiently wet to prevent particle accumulation and fouling in the bed. Adequate wetting of the packing 71 will also maximize catalyst wetting and capture into the liquid phase throughout the packed bed 70. The wetting liquid stream distributor 62 will be spaced apart below the vapor passages 56. The wetting liquid stream distributor 62 and the vapor passages 56 should be disposed on the same side of the bed 70 and preferably above the bed to, in an embodiment, provide downward flow through the bed.

The second wetting liquid stream and the vaporous reactor effluent stream pass together through the bed 70 in a co-current flow arrangement while disengaging catalyst from the vaporous reactor effluent stream to reduce its catalyst loading and transferring the catalyst into the wetting liquid stream to increase its catalyst loading. Particle transfer from the vaporous reactor effluent stream into the wetting liquid stream will occur in the bed 70 below the wetting liquid stream distributor 62.

The second wetting liquid stream with an increased loading of catalyst is separated in a vapor liquid separator 72 below the bed 70 from the vaporous reactor effluent stream with a further decreased loading of catalyst at the bottom of the second chamber 60. In the second chamber 60, the second bed 70 is interposed between the second wetting distributor 62 and the vapor-liquid separator 72.

A chimney tray 74 may be used as the vapor liquid separator 72 to make the separation. The chimney tray 74 may have one or more chimneys 73 each comprising an open tube 75 extending upwardly from the tray aligned with a respective opening or vapor passage 79 in the tray with a cap 76 over a respective open tube. The tube 75 allows a liquid level to develop on the tray 74 which is designed to rise to below the top of the open tube. The cap 76 on the tube 75 prevents descending liquid from passing through the chimney 73 and through the vapor passage 79 in the tray 74. Normally only vaporous reactor effluent passes through the chimney 73 from the second chamber 60 through vapor passage 79 to below the tray 74 and/or to a downstream chamber.

A well 78 at a periphery of the tray 74 collects the liquid which is discharged from a wetting liquid stream outlet 80 from the second chamber 60. The second wetting liquid stream with an increased loading of catalyst is removed in line 82 from the liquid stream outlet 80 and is pumped around to provide the pump around stream in line 65. A portion of the second wetting liquid stream removed at outlet 80 is purged to water treatment in purge line 83. The loading of catalyst in the second wetting liquid stream is determined by the proportions of water added from lines 68 and 65 to make the second wetting stream in line 64 which can depend on the amount of water purged in line 83.

The chimney tray 74 may require agitation or flushing to prevent accumulation of catalyst and disruption of pump performance. Extra nozzles and liquid inlet devices may be provided in the vicinity of the chimney tray 74 to reduce the risk of particulate buildup in stagnant zones of the tray which may otherwise agglomerate catalyst. The chimney tray 74 may be sloped or slanted toward the well 78 to facilitate particle collection to reduce the risk of disruption of pump performance.

In the second chamber 60, the second bed 70 is interposed between the second wetting distributor 62 and the vapor-liquid separator 72. The second chamber 60 in the illustrated embodiment is defined by the outer wall 24, the first vapor liquid separator 42 and the second vapor liquid separator 72.

In an embodiment, a departiculated vaporous reactor effluent stream with a further decreased loading of catalyst to be essentially free of catalyst is passed through at least one passage 79 to a downstream chamber. In an embodiment, the next immediately downstream chamber is an alkaline wash chamber 90. The alkaline wash chamber 90 comprises an alkaline liquid distributor 92 proximate to the vapor passage 79 for admitting the vaporous reactor effluent stream to the alkaline wash chamber 90.

In the alkaline wash chamber 90 the alkaline liquid distributor 92 distributes an aqueous alkaline liquid stream to the vaporous reactor effluent to neutralize and remove the byproduct organic acids, such as acetic acid and formic acid, that are produced in the upstream reactor 202, particularly in an MTO reaction. The acids are chemically neutralized by the alkali, which may be sodium hydroxide, and pass into the aqueous phase from the vapor phase to remove them from the vaporous reactor effluent. The aqueous alkaline liquid stream may have a temperature in the range of about 50° C. to about 65° C.

The alkaline liquid distributor 92 comprises an array of apertured pipes 96 which feed and distribute the alkaline liquid stream from a line 94 across the cross section of the alkaline wash chamber 90 into the departiculated vaporous reactor effluent stream and onto a bed 100 to neutralize organic acid components in the vaporous reactor effluent stream by direct contact with the alkaline liquid stream. The alkaline liquid stream in line 94 may comprise some or all of pump around alkaline liquid in line 95, make-up alkaline liquid in line 98 and final pump around water from line 103 to provide the aqueous alkaline liquid in line 94. The aqueous alkaline liquid in line 94 may comprise an aqueous alkaline solution having a concentration of between about 0.25 and about 2 wt % sodium hydroxide. The make-up alkaline solution in line 98 may comprise about 5 to about 10 wt % sodium hydroxide.

The alkaline liquid distributor 92 may be spaced below a top of the third chamber 90 or the vapor liquid separator 72 and a minimum distance above the bed 100. The typical minimum distance is between about 0.3 and about 2 meters. The bed 100 may comprise a packing 101 which may comprise a grid of adjoining metal corrugated plates stacked in layers to foster circuitous travel through the bed to promote contacting between the liquid and the vapor. The packing 101 in the bed 100 should be fouling-resistant, structured packing for severe service. Random packing may also be used in the bed 100, but it should be fouling resistant. The packing 101 may be the same as that used in first bed 40 and/or the second bed 70.

The alkaline liquid stream and the vaporous reactor effluent stream pass co-currently together through the bed 100 while thoroughly contacting each other to assure adequate neutralization to reduce the acidity of the vaporous reactor effluent stream. In an embodiment, the alkaline liquid stream and the vaporous reactor effluent stream may pass counter currently through the bed 100 while thoroughly contacting each other to assure adequate neutralization to reduce the acidity of the vaporous reactor effluent stream and exiting the third neutralization chamber 90 on opposite sides of the bed.

The alkaline liquid stream is separated from the vaporous reactor effluent stream with a decreased acidity in a vapor liquid separator 102 below the bed 100 at the bottom of the third chamber 90. In the third chamber 90, the third bed 100 is interposed between the alkaline liquid distributor 92 and the vapor-liquid separator 102.

The vapor liquid separator 102 may be structured as a vapor passage 104 that is above a liquid outlet 106 and above a bottom 108 of the third chamber 90. The alkaline liquid stream with an increased concentration of organic salts collects in the bottom 108 of the third alkaline wash chamber 90 and is drawn off through the liquid outlet 106. The liquid outlet 106 may draw the alkaline liquid stream from a well 107 in the bottom 108 of the third alkaline wash chamber 90. A deacidified vaporous reactor effluent stream is removed through the vapor passage 104 at an elevation above the liquid outlet 106 effecting a separation of the vaporous reactor effluent stream and the alkaline liquid stream with an increased organic salt concentration. The vapor passage 104 may be equipped with a baffle 110 above the vapor passage to ensure that descending vapor must reverse direction once below a lower edge of the baffle 110 before passing through the vapor passage 104 to prevent liquid from passing through the vapor passage 104. It is also envisioned that the liquid outlet 106 could be located in the bottom 108 of the alkaline wash chamber 90. In an illustrated embodiment, the alkaline wash chamber 90 is defined by the vapor liquid separator 72, the outer wall 24 and the bottom 108.

The alkaline liquid stream with an increased concentration of organic salts is discharged from the liquid outlet 106 from the alkaline wash chamber 90. The alkaline liquid stream is removed in line 112 from the liquid outlet 106 and is pumped around to provide the pump around stream in line 95. A portion of the alkaline liquid stream removed at outlet 106 is purged to water treatment in a purge line 97. The concentration of alkaline in the alkaline liquid stream in line 94 is determined by the proportions of alkaline solution added from lines 95, 98 and 103 to make the alkaline liquid stream in line 94 which may depend on the proportion of the alkaline liquid stream in line 112 purged in purge line 97. The deacidified vaporous reactor effluent passes from the vapor passage 104 through a line 105 to a downstream chamber 120.

The downstream chamber 120 may be a final wash chamber and it may be in the single vessel 22. The final chamber 120 comprises a final liquid stream distributor 122 and a vaporous reactor effluent inlet 124 in downstream communication with the vapor passage 104 via line 105. In an embodiment, unlike in any of the upstream chambers, the bed 130 is interposed between the vaporous reactor effluent inlet 124 and the final liquid stream distributor 122, so as to directly contact the final liquid stream with the vaporous reactor effluent counter currently.

In the final wash chamber 120, a final wash liquid stream is distributed to the deacidified vaporous reactor effluent stream to finally wash the vaporous reactor effluent stream to remove any residual alkaline solution therefrom. The final liquid distributor 122 comprises an array of apertured pipes 126 which may feed and distribute the final liquid stream into the deacidified vaporous reactor effluent stream and onto the bed 130 to finally wash the vaporous reactor effluent stream by direct contact with the final liquid stream. The final liquid stream in line 125 may comprise some or all of final water in line 115 pumped around from the bottom 128 of the final wash chamber 120 and stripped water from line 113. The final wash liquid stream may have a temperature in the range of about 50° C. to about 65° C.

The final liquid distributor 122 may be located below a top of the final chamber 120 which may be the bottom 108 of the alkaline wash chamber 90 and a minimum distance above the bed 130. The typical minimum distance is about 0.3 to about 2 meters. The bed 130 may comprise a packing 131 which may comprise a grid of adjoining metal corrugated plates stacked in layers to foster circuitous travel through the bed to promote contacting between the liquid and the vapor. The packing 131 in the bed 130 should be fouling-resistant, structured packing for severe service. Random packing may also be used in the bed 130, but it should be fouling resistant. The packing 131 may be the same packing 41, 71 and 101 used in any or all of the beds 40, 70 and 100.

The final liquid stream and the vaporous reactor effluent stream pass counter currently through the bed 130 while thoroughly contacting each other to assure adequate washing of the vaporous reactor effluent stream with water to remove residual alkali.

The final liquid stream passes downwardly through the bed 130 and collects in the bottom 128 of the final chamber 120 which may also be the bottom of the single vessel 22. The final liquid stream with an increased alkaline concentration is discharged from the final chamber 120 through a final liquid outlet 132 which may be in the bottom 128 into the line 134. A portion of the final liquid stream in line 134 is purged in line 136 to provide the stream in line 115. The deacidfied vaporous reactor effluent stream passes upwardly through the bed to provide a dealkalined vaporous reactor effluent stream above the bed. The dealkalined vaporous reactor effluent is discharged from the final chamber 120 through a final vapor outlet 136 above the bed 130 with a decreased alkaline concentration. In the final wash chamber 120, the final bed 130 is interposed between the final vapor outlet 136 and the final liquid outlet 132. The final liquid stream and the vaporous reactor effluent stream are discharged from the final chamber 120 on opposite sides of the bed 130. A product vapor line 140 carries a washed and dealkalined vaporous reactor effluent stream from the quench tower 20 to a product separator for condensation of the water therein and recovery of reactor effluent products.

The final wash chamber 120 is defined by the bottom 108 of the alkaline wash chamber 90, the outer wall 24 and the bottom 128 of the final wash chamber 120 or the single vessel 22 in the illustrated embodiment.

The reactor effluent quench tower 20 described may effectuate three purposes: quench and desuperheat the reactor effluent from the reactor; remove fine particulate catalyst that was not retained in the reactor; and neutralize and remove the byproduct organic acids generated in the upstream catalytic reaction.

Specific Embodiments

While the following is described in conjunction with specific embodiments, it will be understood that this description is intended to illustrate and not limit the scope of the preceding description and the appended claims.

A first embodiment of the disclosure is a process for cooling and removing catalyst from a hot vaporous reactor effluent stream comprising feeding the hot vaporous reactor effluent stream comprising catalyst and a first quench liquid stream to a first quench chamber; directly contacting the hot vaporous reactor effluent stream with the first quench liquid stream to cool the hot reactor effluent stream and wash catalyst therefrom into the first quench liquid stream; passing the first quench liquid stream and the vaporous reactor effluent stream together through a bed while disengaging catalyst from the vaporous reactor effluent stream and transferring catalyst into the first quench liquid stream. An embodiment of the disclosure is one, any or all of prior embodiments in this paragraph up through the first embodiment in this paragraph further comprising spraying the first quench liquid stream upwardly and downwardly in the first quench chamber. An embodiment of the disclosure is one, any or all of prior embodiments in this paragraph up through the first embodiment in this paragraph further comprising separating the first quench liquid stream with an increased loading of catalyst from the vaporous reactor effluent stream with a decreased loading of catalyst. An embodiment of the disclosure is one, any or all of prior embodiments in this paragraph up through the first embodiment in this paragraph further comprising discharging the first quench liquid stream with an increased loading of catalyst from the first quench chamber and passing the vaporous reactor effluent stream with a decreased loading of catalyst to a downstream chamber. An embodiment of the disclosure is one, any or all of prior embodiments in this paragraph up through the first embodiment in this paragraph wherein the downstream chamber includes a second chamber and further comprising directly contacting the vaporous reactor effluent stream with a decreased loading of catalyst with a second wetting liquid stream to wash catalyst therefrom into the second wetting liquid stream in the second chamber; passing the second wetting liquid stream and the vaporous reactor effluent stream together through a bed while disengaging catalyst from the vaporous reactor effluent stream into the second wetting liquid stream; separating the second wetting liquid stream with an increased loading of catalyst from the vaporous reactor effluent stream with a further decreased loading of catalyst; and discharging the second wetting liquid stream with an increased loading of catalyst from the second chamber and passing the vaporous reactor effluent stream with a further decreased loading of catalyst from the second chamber. An embodiment of the disclosure is one, any or all of prior embodiments in this paragraph up through the first embodiment in this paragraph wherein the downstream chamber includes an alkaline wash chamber and further comprising directly contacting the vaporous reactor effluent stream with an alkaline liquid stream to neutralize acidic components therein in the alkaline wash chamber; passing the alkaline liquid stream and the vaporous reactor effluent stream together through a bed; separating the alkaline liquid stream from the vaporous reactor effluent stream with a decreased acidity; and discharging the alkaline liquid stream from the alkaline wash chamber and passing the vaporous reactor effluent stream with decreased acidity from the alkaline wash chamber. An embodiment of the disclosure is one, any or all of prior embodiments in this paragraph up through the first embodiment in this paragraph wherein the downstream quench chamber includes a final chamber and further comprising directly contacting the vaporous reactor effluent stream with a final liquid stream to wash the reactor effluent stream in the final chamber; passing the final liquid stream and the vaporous reactor effluent stream counter currently through a bed; discharging the final liquid stream and the vaporous reactor effluent stream from the final chamber on opposite sides of the bed.

A second embodiment of the disclosure is an apparatus for cooling and removing catalyst from a hot vaporous reactor effluent stream comprising a first quench chamber having a reactor effluent inlet in downstream communication with the reactor and a quench liquid stream distributor, a bed for disengaging catalyst from the hot vaporous reactor effluent stream and a vapor-liquid separator comprising a quench liquid stream outlet from the first quench chamber and a vapor passage for passing the vaporous reactor effluent to a downstream chamber, the reactor effluent inlet and the quench liquid steam distributor being disposed on the same side of the bed. An embodiment of the disclosure is one, any or all of prior embodiments in this paragraph up through the second embodiment in this paragraph wherein the quench liquid stream distributor comprises nozzles directed upwardly and downwardly. An embodiment of the disclosure is one, any or all of prior embodiments in this paragraph up through the second embodiment in this paragraph further comprising a wetting liquid stream distributor and the reactor effluent inlet being interposed between the quench liquid stream distributor and the wetting liquid stream distributor. An embodiment of the disclosure is one, any or all of prior embodiments in this paragraph up through the second embodiment in this paragraph wherein the downstream chamber comprises a liquid stream distributor proximate to a vapor passage for admitting the vaporous reactor effluent stream to the downstream chamber, a vapor-liquid separator and a bed interposed between the liquid stream distributor and the vapor-liquid separator. An embodiment of the disclosure is one, any or all of prior embodiments in this paragraph up through the second embodiment in this paragraph wherein the downstream chamber comprises a liquid stream distributor, a vaporous reactor effluent inlet in downstream communication with the vapor passage and a bed interposed between the vaporous reactor effluent inlet and the liquid stream distributor. An embodiment of the disclosure is one, any or all of prior embodiments in this paragraph up through the second embodiment in this paragraph wherein the first quench chamber and the downstream chamber are in separate vessels.

A third embodiment of the disclosure is a process for cooling and removing catalyst from a hot vaporous reactor effluent stream comprising feeding the hot vaporous reactor effluent stream comprising catalyst and a first quench liquid stream to a first quench chamber; directly contacting the hot vaporous reactor effluent stream with the first quench liquid stream to cool the hot reactor effluent stream and wash catalyst therefrom into the first quench liquid stream; passing the first quench liquid stream and the vaporous reactor effluent stream together through a first bed while disengaging catalyst from the vaporous reactor effluent stream and transferring catalyst into the first quench liquid stream; passing the vaporous reactor effluent stream with a decreased loading of catalyst to a final chamber; directly contacting the vaporous reactor effluent stream with a final liquid stream to wash the vaporous reactor effluent stream in the final chamber; passing the final liquid stream and the vaporous reactor effluent stream counter currently through a second bed; and discharging the final liquid stream and the vaporous reactor effluent stream from the final chamber on opposite sides of the bed. An embodiment of the disclosure is one, any or all of prior embodiments in this paragraph up through the third embodiment in this paragraph further comprising spraying the first quench liquid stream upwardly and downwardly in the first quench chamber. An embodiment of the disclosure is one, any or all of prior embodiments in this paragraph up through the third embodiment in this paragraph further comprising separating the first quench liquid stream with an increased loading of catalyst from the vaporous reactor effluent stream with a decreased loading of catalyst. An embodiment of the disclosure is one, any or all of prior embodiments in this paragraph up through the third embodiment in this paragraph further comprising discharging the first quench liquid stream with an increased loading of catalyst from the first quench chamber. An embodiment of the disclosure is one, any or all of prior embodiments in this paragraph up through the third embodiment in this paragraph further comprising passing the vaporous reactor effluent stream with a decreased loading of catalyst to a second chamber before passing it to the final chamber; directly contacting the vaporous reactor effluent stream with a decreased loading of catalyst with a wetting liquid stream to wash catalyst from the vaporous reactor effluent stream into the second wetting liquid stream in the second quench chamber; passing the second quench wetting stream and the vaporous reactor effluent stream together through a bed while disengaging catalyst from the vaporous reactor effluent stream into the second wetting liquid stream; separating the second wetting liquid stream with an increased loading of catalyst from the vaporous reactor effluent stream with a further decreased loading of catalyst; and discharging the second wetting liquid stream with an increased loading of catalyst from the second chamber and passing the vaporous reactor effluent stream with a further decreased loading of catalyst to a downstream chamber. An embodiment of the disclosure is one, any or all of prior embodiments in this paragraph up through the third embodiment in this paragraph wherein the downstream chamber includes an alkaline wash chamber and further comprising directly contacting the vaporous reactor effluent stream with a decreased loading of catalyst with an alkaline wash liquid stream to neutralize acidic components therein in the alkaline wash chamber; passing the alkaline wash liquid stream and the vaporous reactor effluent stream together through a bed; separating the alkaline wash liquid stream from the vaporous reactor effluent stream with a decreased acidity; and discharging the alkaline wash liquid stream from the alkaline wash chamber and passing the vaporous reactor effluent stream with decreased acidity to the final chamber.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for cooling and removing catalyst from a hot vaporous reactor effluent stream comprising:
feeding said hot vaporous reactor effluent stream comprising catalyst and a first quench liquid stream to a first quench chamber;
directly contacting said hot vaporous reactor effluent stream with said first quench liquid stream in a co-current flow, to cool said hot reactor effluent stream and wash catalyst therefrom into said first quench liquid stream;
passing said first quench liquid stream and said vaporous reactor effluent stream together through a bed while disengaging catalyst from said vaporous reactor effluent stream and transferring catalyst into said first quench liquid stream.

2. The process of claim 1 further comprising spraying said first quench liquid stream upwardly and downwardly in said first quench chamber.

3. The process of claim 1 further comprising separating said first quench liquid stream with an increased loading of catalyst from said vaporous reactor effluent stream with a decreased loading of catalyst.

4. The process of claim 3 further comprising discharging said first quench liquid stream with an increased loading of catalyst from said first quench chamber and passing said vaporous reactor effluent stream with a decreased loading of catalyst to a downstream chamber.

5. The process of claim 4 wherein said downstream chamber includes a second chamber and further comprising directly contacting said vaporous reactor effluent stream with a decreased loading of catalyst with a second wetting liquid stream to wash catalyst therefrom into said second wetting liquid stream in said second chamber; passing said second wetting liquid stream and said vaporous reactor effluent stream together through a bed while disengaging catalyst from said vaporous reactor effluent stream into said second wetting liquid stream; separating said second wetting liquid stream with an increased loading of catalyst from said vaporous reactor effluent stream with a further decreased loading of catalyst; and discharging said second wetting liquid stream with an increased loading of catalyst from said second chamber and passing said vaporous reactor effluent stream with a further decreased loading of catalyst from said second chamber.

6. The process of claim 4 wherein said downstream chamber includes an alkaline wash chamber and further comprising directly contacting said vaporous reactor effluent stream with an alkaline liquid stream to neutralize acidic components therein in said alkaline wash chamber; passing said alkaline liquid stream and said vaporous reactor effluent stream together through a bed; separating said alkaline liquid stream from said vaporous reactor effluent stream with a decreased acidity; and discharging said alkaline liquid stream from said alkaline wash chamber and passing said vaporous reactor effluent stream with decreased acidity from said alkaline wash chamber.

7. The process of claim 4 wherein said downstream chamber includes an alkaline wash chamber and further comprising directly contacting said vaporous reactor effluent stream with an alkaline liquid stream to neutralize acidic components therein in said alkaline wash chamber; passing said alkaline liquid stream and said vaporous reactor effluent stream counter currently through a bed; separating said alkaline liquid stream from said vaporous reactor effluent stream with a decreased acidity; and discharging said alkaline liquid stream from said alkaline wash chamber and passing said vaporous reactor effluent stream with decreased acidity from said alkaline wash chamber.

8. The process of claim 4 wherein said downstream quench chamber includes a final chamber and further comprising directly contacting said vaporous reactor effluent stream with a final liquid stream to wash said reactor effluent stream in said final chamber; passing said final liquid stream and said vaporous reactor effluent stream counter currently through a bed; discharging said final liquid stream and said vaporous reactor effluent stream from said final chamber on opposite sides of said bed.

9. A process for cooling and removing catalyst from a hot vaporous reactor effluent stream comprising:
feeding said hot vaporous reactor effluent stream comprising catalyst and a first quench liquid stream to a first quench chamber;
directly contacting said hot vaporous reactor effluent stream with said first quench liquid stream to cool said hot reactor effluent stream and wash catalyst therefrom into said first quench liquid stream and distributing a first wetting liquid stream to further capture catalyst and ensure adequate wetting in a first bed;
passing said first quench liquid stream, said first wetting liquid stream and said vaporous reactor effluent stream together through said first bed while disengaging catalyst from said vaporous reactor effluent stream and transferring catalyst into said first quench liquid stream;
passing said vaporous reactor effluent stream with a decreased loading of catalyst to a final chamber;
directly contacting said vaporous reactor effluent stream with a final liquid stream to wash said vaporous reactor effluent stream in said final chamber
passing said final liquid stream and said vaporous reactor effluent stream counter currently through a second bed; and
discharging said final liquid stream and said vaporous reactor effluent stream from said final chamber on opposite sides of said bed.

10. The process of claim 9 further comprising spraying said first quench liquid stream upwardly and downwardly in said first quench chamber.

11. The process of claim 9 further comprising separating said first quench liquid stream with an increased loading of catalyst from said vaporous reactor effluent stream with a decreased loading of catalyst.

12. The process of claim 11 further comprising discharging said first quench liquid stream with an increased loading of catalyst from said first quench chamber.

13. The process of claim 11 further comprising passing said vaporous reactor effluent stream with a decreased loading of catalyst to a second chamber before passing it to the final chamber; directly contacting said vaporous reactor effluent stream with a decreased loading of catalyst with a second wetting liquid stream to wash catalyst from said vaporous reactor effluent stream into said second wetting liquid stream in said second quench chamber; passing said second wetting liquid stream and said vaporous reactor effluent stream together through a bed while disengaging catalyst from said vaporous reactor effluent stream into said second wetting liquid stream; separating said second wetting liquid stream with an increased loading of catalyst from said vaporous reactor effluent stream with a further decreased loading of catalyst; and discharging said second wetting liquid stream with an increased loading of catalyst from said second chamber and passing said vaporous reactor effluent stream with a further decreased loading of catalyst to a downstream chamber.

14. The process of claim 13 wherein said downstream chamber includes an alkaline wash chamber and further comprising directly contacting said vaporous reactor effluent stream with a decreased loading of catalyst with an alkaline wash liquid stream to neutralize acidic components therein in said alkaline wash chamber; passing said alkaline wash liquid stream and said vaporous reactor effluent stream together through a bed; separating said alkaline wash liquid stream from said vaporous reactor effluent stream with a decreased acidity; and discharging said alkaline wash liquid stream from said alkaline wash chamber and passing said vaporous reactor effluent stream with decreased acidity to said final chamber.

* * * * *